United States Patent
Hirakawa (10) Patent No.: US 10,475,235 B2
(45) Date of Patent: Nov. 12, 2019

(54) THREE-DIMENSIONAL IMAGE PROCESSING APPARATUS, THREE-DIMENSIONAL IMAGE PROCESSING METHOD, AND THREE-DIMENSIONAL IMAGE PROCESSING PROGRAM

(71) Applicant: FUJIFILM Corporation, Tokyo (JP)

(72) Inventor: Shinnosuke Hirakawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/906,235

(22) Filed: Feb. 27, 2018

(65) Prior Publication Data

US 2018/0286108 A1 Oct. 4, 2018

(30) Foreign Application Priority Data

Mar. 29, 2017 (JP) ................................. 2017-065096
Sep. 22, 2017 (JP) ................................. 2017-182196

(51) Int. Cl.
*G06T 15/20* (2011.01)
*H04N 7/18* (2006.01)
(Continued)

(52) U.S. Cl.
CPC .......... *G06T 15/205* (2013.01); *A61B 1/2676* (2013.01); *A61B 34/20* (2016.02); *G06T 7/0012* (2013.01); *G06T 19/003* (2013.01); *H04N 7/183* (2013.01); *A61B 2034/2057* (2016.02); *A61B 2034/2065* (2016.02); *G06T 2207/10068* (2013.01); *G06T 2207/30061* (2013.01); *G06T 2210/41* (2013.01)

(58) Field of Classification Search
None
See application file for complete search history.

(56) References Cited

U.S. PATENT DOCUMENTS

2004/0249270 A1* 12/2004 Kondo .................... G06T 15/08
600/425
2009/0148013 A1* 6/2009 Metaxas ............... G06T 7/0012
382/128
2015/0057498 A1 2/2015 Akimoto et al.

FOREIGN PATENT DOCUMENTS

JP 11-120327 A 4/1999
JP 2013-192741 A 9/2013
JP WO 2014/141968 A1 9/2014

* cited by examiner

*Primary Examiner* — Said Broome
(74) *Attorney, Agent, or Firm* — Birch, Stewart, Kolasch & Birch, LLP (57) ABSTRACT

A three-dimensional image processing apparatus includes a three-dimensional image acquisition unit that acquires a three-dimensional image obtained by imaging a test object; a graphical structure generation unit that generates a graphical structure of a tubular structure included in the three-dimensional image; a contour information acquisition unit that acquires contour information on the tubular structure at each point on the graphical structure; a viewpoint information acquisition unit that acquires viewpoint information in the tubular structure; a projection point specification unit that specifies projection points from respective points on the graphical structure on the basis of the viewpoint information and the graphical structure; and a projection image generation unit that generates a projection image obtained by projecting the contour information at the projection points on a two-dimensional plane.

13 Claims, 8 Drawing Sheets

(51) Int. Cl.
*G06T 7/00* (2017.01)
*G06T 19/00* (2011.01)
*A61B 1/267* (2006.01)
*A61B 34/20* (2016.01)

THREE-DIMENSIONAL IMAGE PROCESSING APPARATUS, THREE-DIMENSIONAL IMAGE PROCESSING METHOD, AND THREE-DIMENSIONAL IMAGE PROCESSING PROGRAM

CROSS-REFERENCE TO RELATED APPLICATIONS

This application claims priority from Japanese Patent Application No. 2017-065096, filed on Mar. 29, 2017, and Japanese Patent Application No. 2017-182196, filed on Sep. 22, 2017, the disclosure of which are incorporated by reference herein in these entirety.

BACKGROUND

Field of the Invention

The present invention relates to a three-dimensional image processing apparatus, a three-dimensional image processing method, and a three-dimensional image processing program for supporting insertion of an endoscope into a pipe line in the body such as a bronchial tube using a three-dimensional image obtained by imaging a test object.

Related Art

Recently, along with advances of an imaging apparatus, resolution of image data obtained by imaging using an imaging apparatus has been enhanced, and detailed analysis of a test object has become possible on the basis of the image data. For example, multi detector-row computed tomography (CT) is able to capture a plurality of tomographic images all at once, and is able to capture tomographic images with a thin slice thickness. As the slice thickness becomes thin, resolution of a three-dimensional image in which a plurality of tomographic images is layered in a body axis direction is enhanced, to thereby make it possible to obtain a detailed three-dimensional image. By displaying and analyzing such a three-dimensional image, it is possible to find out lesion or the like that has not easily been found so far.

As one display method using the above-described three-dimensional image, a virtual endoscope display method is used (for example, see WO2014/141968A and JP1999-120327A (JP-H11-120327A)). The virtual endoscope display method refers to a method for setting a viewpoint position inside a lumen, generating a perspective projection image on the basis of the viewpoint position, and displaying the perspective projection image. In the virtual endoscope display method, as a user sequentially changes viewpoint positions, it is possible to provide an image as if a camera of the endoscope performs imaging while moving inside the body.

Particularly, in bronchoscopy that is an inspection using an endoscope, since divergence of bronchial tubes is extremely complicated, insertion of the endoscope is performed while referring to the above-described virtual endoscope display as a "map". In this case, since it is laborious to sequentially change the virtual endoscope display method manually to match movement of an actual endoscope, a method for estimating which place in the body a tip of the endoscope is located at to create a virtual endoscope image.

For example, WO2014/141968A proposes a method for performing a registration process of a virtual endoscope image and an endoscope image that is actually captured using an endoscope so as to estimate a tip position of the endoscope.

Here, in order to estimate the tip position of the endoscope for navigation, it is necessary to generate virtual endoscope images from a plurality of viewpoints, and to perform a registration process of the virtual endoscope images and actually captured endoscope images to select most similar images.

However, in order to enhance estimation accuracy or stability of a tip position of an endoscope, it is necessary to generate a large amount of virtual endoscope images, but a volume rendering process that is a process of generating virtual endoscope images takes a lot of time.

JP2013-192741A discloses a technique for generating a graphical structure from a three-dimensional image of bronchial tubes, and generating, with respect to each of a plurality of divergent points included in the graphical structure, a projection image obtained by projecting divergence destinations from the divergent point on a two-dimensional plane including the divergent point, but since the projection image is a schematic image indicating the divergence destinations and is not an image that correctly represents shapes or the like of holes of bronchial tubes, the projection image is not suitable for the above-described registration process with respect to the endoscope image.

An object of the present invention is to provide a three-dimensional image processing apparatus, a three-dimensional image processing method, and a three-dimensional image processing program capable of generating, through a high-speed process, an image in which a direct feature is remained so that a registration process with respect to an endoscope image can be performed.

SUMMARY

According to an aspect of the present invention, there is provided a three-dimensional image processing apparatus comprising: a three-dimensional image acquisition unit that acquires a three-dimensional image obtained by imaging a test object; a graphical structure generation unit that generates a graphical structure of a tubular structure included in the three-dimensional image; a contour information acquisition unit that acquires contour information on the tubular structure at each point on the graphical structure; a viewpoint information acquisition unit that acquires viewpoint information in the tubular structure; a projection point specification unit that specifies projection points from respective points on the graphical structure on the basis of the viewpoint information and the graphical structure; and a projection image generation unit that generates a projection image obtained by projecting the contour information at the projection points on a two-dimensional plane.

In the three-dimensional image processing apparatus according to the present invention, the projection point specification unit may specify one point on the graphical structure as a starting point, may specify points included in a preset range as projection candidate points while following the graphical structure from the starting point, and may specify the projection points from the projection candidate points.

In the three-dimensional image processing apparatus according to the present invention, the projection point specification unit may specify the projection points on the basis of shape information of the contour information.

In the three-dimensional image processing apparatus according to the present invention, the projection image generation unit may acquire information on branches to which the projection points belong, and may add the information on the branches to the projection image.

The three-dimensional image processing apparatus according to the present invention may further comprise: a viewpoint information estimation unit that estimates, on the basis of a result of a registration process between the projection image and an image different from the projection image and viewpoint information on the projection image, viewpoint information on the different image.

The three-dimensional image processing apparatus according to the present invention may further comprise: a contour information estimation unit that estimates, on the basis of a result of a registration process between the projection image and an image different from the projection image, contour information included in the different image corresponding to the contour information included in the projection image.

In the three-dimensional image processing apparatus according to the present invention, the image different from the projection image may be a two-dimensional image obtained by imaging the test object.

In the three-dimensional image processing apparatus according to the present invention, the two-dimensional image may be an image captured by an endoscope.

The three-dimensional image processing apparatus according to the present invention may further comprise: a display controller that causes a display device to display the projection image.

In the three-dimensional image processing apparatus according to the present invention, the tubular structure may be a bronchial tube.

According to another aspect of the present invention, there is provided a three-dimensional image processing method comprising: acquiring a three-dimensional image obtained by imaging a test object; generating a graphical structure of a tubular structure included in the three-dimensional image; acquiring contour information on the tubular structure at each point on the graphical structure; acquiring viewpoint information in the tubular structure; specifying projection points from respective points on the graphical structure on the basis of the viewpoint information and the graphical structure; and generating a projection image obtained by projecting the contour information at the projection points on a two-dimensional plane.

According to still another aspect of the present invention, there is provided a three-dimensional image processing program that causes a computer to function as: a three-dimensional image acquisition unit that acquires a three-dimensional image obtained by imaging a test object; a graphical structure generation unit that generates a graphical structure of a tubular structure included in the three-dimensional image; a contour information acquisition unit that acquires contour information on the tubular structure at each point on the graphical structure; a viewpoint information acquisition unit that acquires viewpoint information in the tubular structure; a projection point specification unit that specifies projection points from respective points on the graphical structure on the basis of the viewpoint information and the graphical structure; and a projection image generation unit that generates a projection image obtained by projecting the contour information at the projection points on a two-dimensional plane.

According to still another aspect of the present invention, there is provided a three-dimensional image processing apparatus comprising: a memory that stores a command to be executed by a computer; and a processor that is configured to execute the stored command, in which the processor is configured to execute a process of acquiring a three-dimensional image obtained by imaging a test object and generating a graphical structure of a tubular structure included in the three-dimensional image; a process of acquiring contour information on the tubular structure at each point on the graphical structure; a process of acquiring viewpoint information in the tubular structure; a process of specifying projection points from respective points on the graphical structure on the basis of the viewpoint information and the graphical structure; and a process of generating a projection image obtained by projecting the contour information at the projection points on a two-dimensional plane.

According to the three-dimensional image processing apparatus, the three-dimensional image processing method, and the three-dimensional image processing program of the present invention, a three-dimensional image obtained by imaging a test object is acquired; a graphical structure of a tubular structure included in the three-dimensional image is generated; and contour information on the tubular structure at each point on the graphical structure is acquired. Further, viewpoint information in the tubular structure is acquired; projection points are specified from respective points on the graphical structure on the basis of the viewpoint information and the graphical structure; and a projection image obtained by projecting the contour information at the projection points on a two-dimensional plane is generated.

Accordingly, it is possible to generate, through a high-speed process, a projection image in which a direct feature is remained so that a registration process with respect to an endoscope image can be performed.

DETAILED DESCRIPTION

Figure 1:
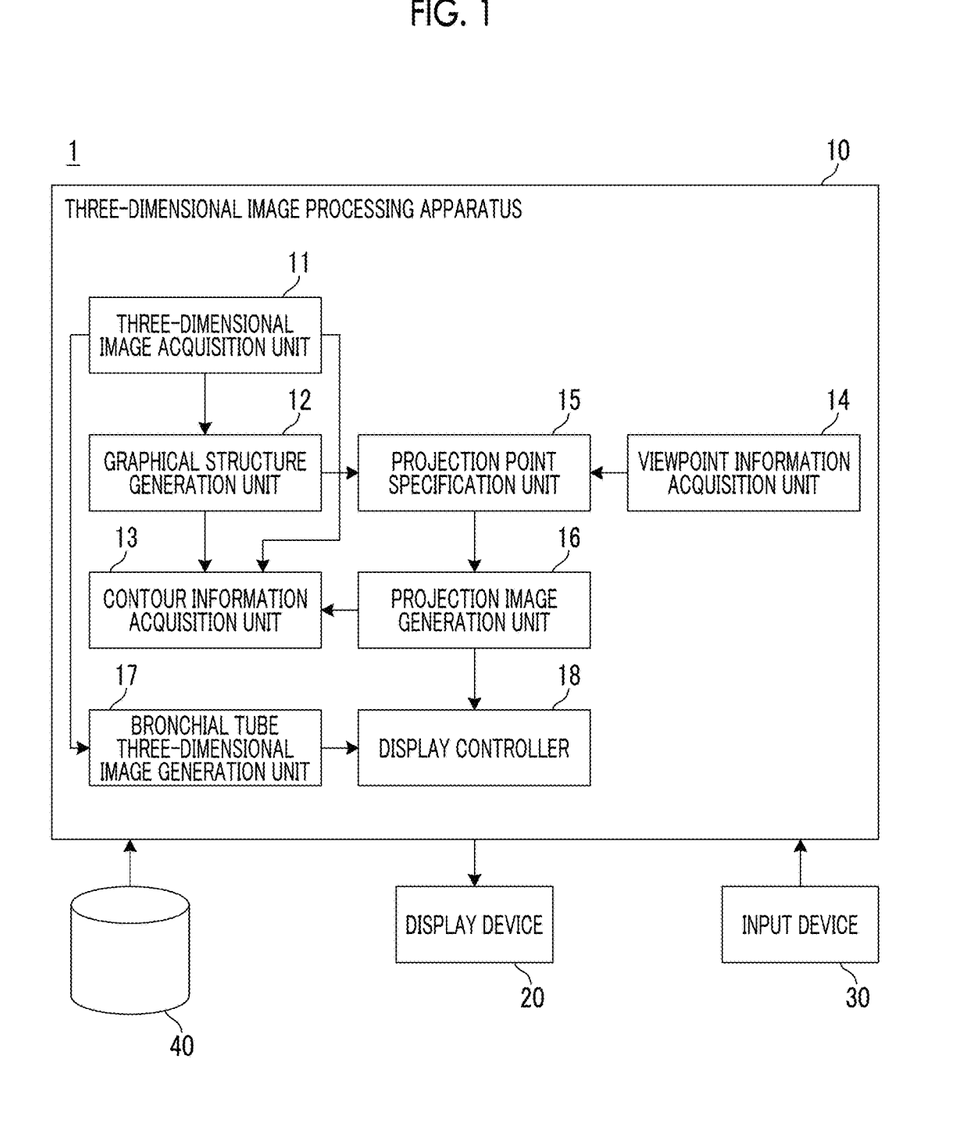
FIG. 1 is a block diagram showing a schematic configuration of an endoscope image diagnosis support system using an embodiment of a three-dimensional image processing apparatus according to the present invention.

Hereinafter, an endoscope image diagnosis support system using an embodiment of a three-dimensional image processing apparatus, a three-dimensional image processing method, and a three-dimensional image processing program according to the present invention will be described in detail with reference to the accompanying drawings. FIG. 1 is a block diagram showing a schematic configuration of the endoscope image diagnosis support system according to this embodiment.

An endoscope image diagnosis support system 1 of this embodiment includes a three-dimensional image processing apparatus 10, a display device 20, an input device 30, and a three-dimensional image storage server 40, as shown in FIG. 1.

The three-dimensional image processing apparatus 10 is configured by installing a three-dimensional image processing program of this embodiment to a computer.

Further, the three-dimensional image processing apparatus 10 includes a central processing unit (CPU), a storage device such as a semiconductor memory, a hard disk or a solid state drive (SSD) in which the above-mentioned three-dimensional image processing program is installed, and the like.

A three-dimensional image acquisition unit 11, a graphical structure generation unit 12, a contour information acquisition unit 13, a viewpoint information acquisition unit 14, a projection point specification unit 15, a projection image generation unit 16, a bronchial tube three-dimensional image generation unit 17, and a display controller 18 shown in FIG. 1 are formed by the above-mentioned hardware. Further, as the three-dimensional image processing program installed in the hard disk is executed by the CPU, the respective units are respectively operated.

The three-dimensional image acquisition unit 11 acquires a three-dimensional image of a test object that is captured in advance, for example, before an operation, or before an inspection using an endoscope apparatus. As the three-dimensional image, for example, volume data that is re-configured of slice data output from a CT apparatus, a magnetic resonance imaging (MRI) apparatus, or the like, volume data output from a multi slice (MS) CT apparatus and a cone beam CT apparatus, or the like, may be used.

Three-dimensional images are stored in advance together with identification information on test objects in the three-dimensional image storage server 40, and the three-dimensional image acquisition unit 11 reads out a three-dimensional image corresponding to identification information on a test object input through the input device 30 from the three-dimensional image storage server 40.

The graphical structure generation unit 12 receives an input of a three-dimensional image acquired by the three-dimensional image acquisition unit 11, and generates a graphical structure of a tubular structure included in the input three-dimensional image. In this embodiment, a graphical structure of bronchial tubes is generated as the graphical structure of the tubular structure. Hereinafter, an example of a method for generating the graphical structure will be described.

In the bronchial tubes included in the three-dimensional image, it may be considered that pixels for the inside of the bronchial tubes correspond to an air region and are thus displayed as a region indicating low CT values (pixel values) on a CT image but a bronchial tube wall is a tubular or cylindrical structure of indicating relatively high CT values. Accordingly, by performing shape structure analysis based on distribution of CT values for each pixel, it is possible to extract bronchial tubes.

The bronchial tubes are diverged in multiple stages, and diameters of the bronchial tubes become smaller as they are close to their ends. In order to detect bronchial tubes having different sizes, Gaussian pyramid images obtained by multiple-resolution-converting three-dimensional images, that is, a plurality of three-dimensional images of different resolutions are generated in advance, a detection algorithm is scanned for each of the generated Gaussian pyramid images to detect tubular structures having different sizes.

First, a Hessian matrix of respective pixels of a three-dimensional image of each resolution is calculated, and it is determined whether the pixels are pixels for the inside of a tubular structure from a magnitude relationship of eigenvalues in the Hessian matrix. The Hessian matrix refers to a matrix in which two-stage partial differential coefficients of density values in respective axes (x-axis, y-axis, and z-axis of a three-dimensional image) directions are elements, and is a 3×3 matrix as in the following expression.

$$\nabla^2 I = \begin{bmatrix} I_{xx} & I_{xy} & I_{xz} \\ I_{xx} & I_{xy} & I_{xz} \\ I_{xx} & I_{xy} & I_{xz} \end{bmatrix} \quad I_{xx} = \frac{\delta^2 I}{\delta x^2}, I_{xy} = \frac{\delta^2 I}{\delta x \delta y^2}, \ldots$$

When eigenvalues of the Hessian matrix in an arbitrary pixel are λ1, λ2, and λ3, in a case where two eigenvalues among the eigenvalues are large and one eigenvalue is close to 0, for example, when λ3, λ2≫1, and λ1≅0 are satisfied, it is known that the pixel represents a tubular structure. Further, an eigenvector corresponding to a minimum eigenvalue (λ1≅0) in the Hessian matrix matches a main axis direction of the tubular structure.

Although the bronchial tubes may be displayed in the graphical structure, it is not essential that the tubular structure extracted in this way is detected as one graphical structure in which all tubular structures are connected to each other, due to the influence of tumors, or the like. Thus, after discrimination of all the three-dimensional images is completed, by evaluating whether the detected tubular structure is present within a predetermined distance, and whether an angle formed by a direction of a basic line that connects arbitrary points on two extracted tubular structures and a main axis direction of each tubular structure is equal to or smaller than a predetermined angle, it is determined whether a plurality of tubular structures is connected to each other, and a connection relationship between the extracted tubular structures is reconstructed. With the reconstruction, the extraction of the graphical structure of the bronchial tubes is completed.

Figure 2:
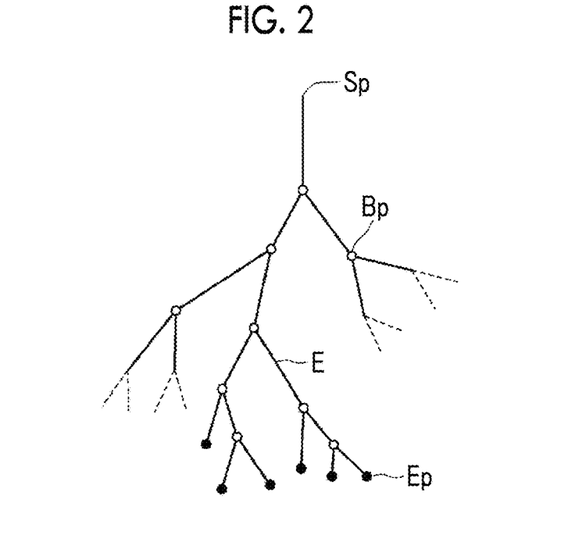
FIG. 2 is a diagram showing an example of a graphical structure.

Further, by classifying the extracted graphical structure into a starting point, an end point, a divergent point, and branches and by connecting the starting point, the end point, and the divergent point using the branches, it is possible to obtain the graphical structure indicating the bronchial tubes. In this embodiment, a feature value such as the diameter of a bronchial tube at each position in the graphical structure or the length of each branch (a length between divergent points of a bronchial tube) is also acquired together with the graphical structure. FIG. 2 shows an example of a graphical structure. In FIG. 2, Sp represents a starting point. Further, a divergent point Bp is indicated by a white circle, an end point Ep is indicated by a black circle, and a branch E is indicated by a line.

The method for generating the graphical structure is not limited to the above-described method, and instead, other known methods may be used.

Figure 3:
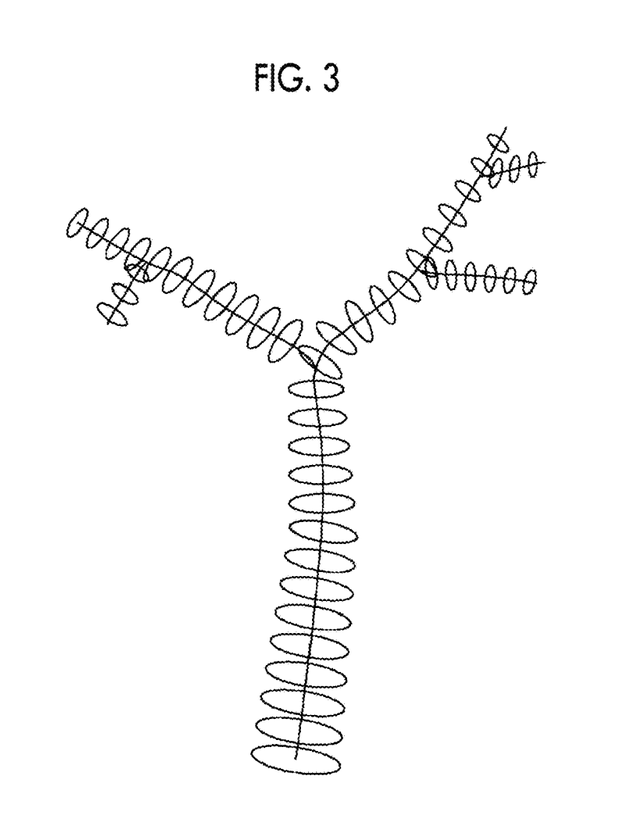
FIG. 3 is a diagram showing an example of contour information on bronchial tubes at respective points on the graphical structure.
Figure 4:
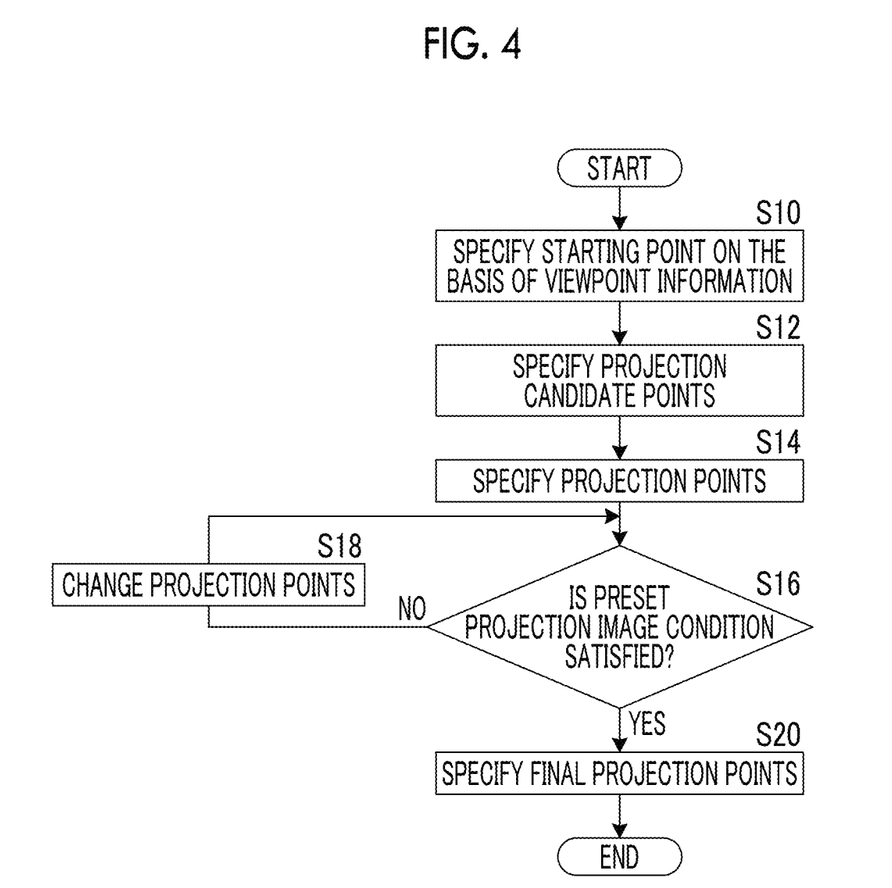
FIG. 4 is a flowchart illustrating a method for specifying projection points.

The contour information acquisition unit 13 acquires contour information on bronchial tubes at respective points on a graphical structure. The contour information acquisition unit 13 of this embodiment acquires contour information on the tubular structures detected when the graphical structure of the bronchial tubes is generated as described above. In a case where the contour information is acquired with respect to respective points on a graphical structure, an interval between the respective points may be arbitrarily set to an interval smaller than that between branch points of bronchial tubes. For example, it is preferable that the interval is set to about 1 mm to 2 mm. FIG. 3 is a diagram showing an example of contour information on bronchial tubes at respective points on a graphical structure. In FIG. 3, the graphical structure of the bronchial tubes is also included.

The viewpoint information acquisition unit 14 acquires viewpoint information in bronchial tubes. The viewpoint information may be arbitrarily set and input using the input device 30 from a user, and the viewpoint information acquisition unit 14 acquires viewpoint information received through the input device 30. The setting and input of the viewpoint information may be performed by designation of a user using the input device 30 such as a mouse on a three-dimensional image of bronchial tubes displayed on the display device 20, for example.

In this embodiment, the viewpoint information is set and input by a user, but the present invention is not limited thereto. For example, the viewpoint information may be automatically set on the basis of a preset condition. Specifically, the viewpoint information may be set in a base end part of a bronchial tube, or may be set at the first divergence from the base end part, for example.

The projection point specification unit 15 specifies one point on a graphical structure as a starting point on the basis of the viewpoint information, and specifies projection points from respective points on the graphical structure while following the graphical structure from the starting point. Hereinafter, the specification of the projection points in the projection point specification unit 15 will be described with reference to a flowchart shown in FIG. 4, and FIGS. 5 to 10.

Figure 5:
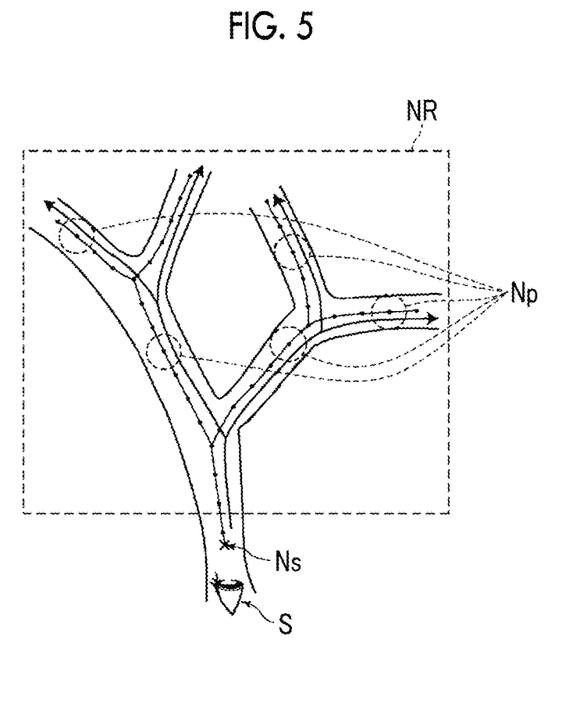
FIG. 5 is a diagram illustrating the method for specifying the projection points.

First, the projection point specification unit 15 specifies a point on a graphical structure that is closest to viewpoint information S that is set and input by a user, as shown in FIG. 5, as a starting point Ns (S10). Then, the projection point specification unit 15 specifies points included in a preset range NR as projection candidate points while following the graphical structure from the starting point Ns toward a downstream side (a side opposite to a base end side) of bronchial tubes (S12). As the range NR, for example, a range at a preset distance from the starting point Ns or a range in which the number of divergent points passed when following the graphical structure from the starting point Ns becomes a preset number may be set.

Next, the projection point specification unit 15 specifies partial projection points from the plurality of projection candidate points included in the preset range NR on the basis of a preset projection point condition (S14). As the preset condition, for example, a condition that a central point, a first point or a final point of each branch in the graphical structure in the range NR is specified as a projection point may be used. The first point and the final point refer to a first point and a final point of each side when following the graphical structure toward the downstream side. Further, with respect to each branch in the graphical structure in the range NR, a first point that is spaced from a divergent point by a preset distance or longer may be specified as a projection point. FIG. 5 shows an example of projection points Np specified in S14, indicated by dot-line round circles.

Figure 6:
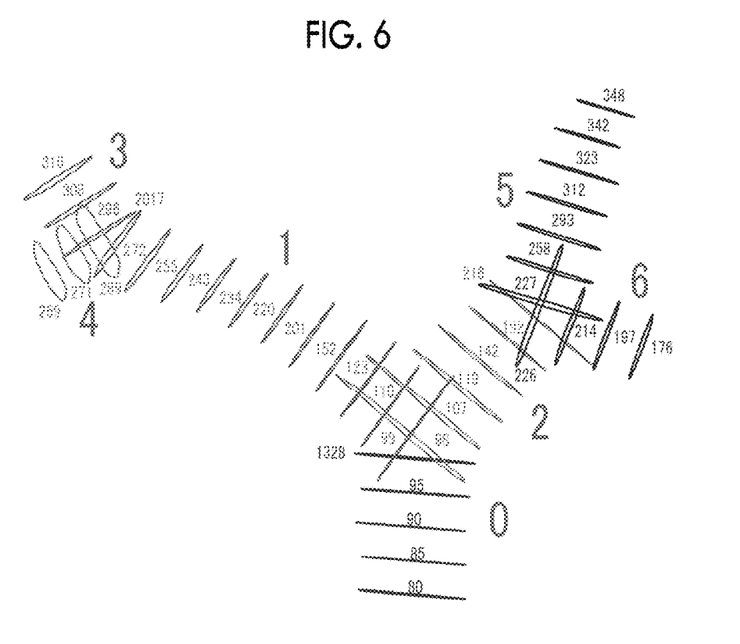
FIG. 6 is a diagram showing an example of contour information at respective points on the graphical structure.

Then, the projection point specification unit 15 checks whether the projection points specified in S14 satisfy a preset projection image condition (S16). FIG. 6 is a diagram showing an example of contour information at respective points on the graphical structure in the range NR. In FIG. 6, for ease of illustration, contour information at a part of the points is not shown. Further, numerical values of 0 to 6 shown in FIG. 6 are branch numbers added to respective branches, and a numerical value shown in the vicinity of each piece of contour information is a node number given to each point on the graphical structure. Here, a method for specifying projection points, for example, in a case where the above-described starting point Ns is in a node 80 shown in FIG. 6 will be described.

Figure 7:
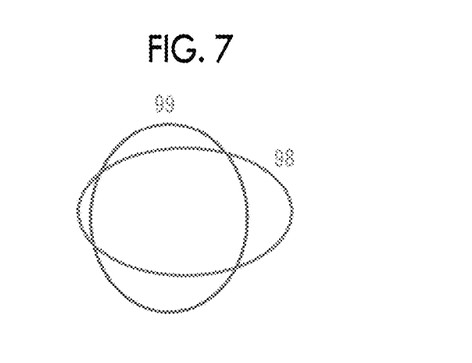
FIG. 7 is a diagram showing an example of a projection image.

First, in a case where the projection points specified in S14 correspond to a node 98 and a node 99 shown in FIG. 6, a projection image generated by projecting contour information at the two node points on a two-dimensional plane becomes a projection image as the projection image shown in FIG. 7. The two-dimensional plane is a plane orthogonal to a body direction of a test object. In the projection image shown in FIG. 7, since two pieces of contour information overlap each other, the projection image is not preferable as a projection image. This is because the projection points specified in S14 are excessively close to the divergent point.

Thus, in a case where two pieces of contour information overlap each other as shown in FIG. 7, the projection point specification unit 15 changes projection points, generates a projection image again using contour information at the projection points after the change, and checks whether the pieces of contour information in the projection image overlap each other. Specifically, the projection point specification unit 15 changes at least one of the projection points of the node 98 and the node 99 to a projection point distant from the divergent point, and generates a projection image again using contour information at projection points after the change. For example, the projection point of the node 98 is changed into a projection point of a node 107, and the projection point of the node 99 is changed into a projection point of a node 110.

Figure 8:
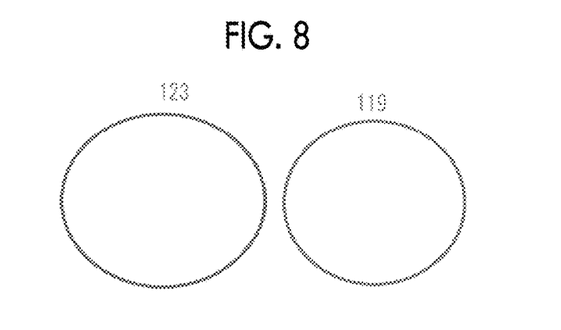
FIG. 8 is a diagram showing an example of a projection image generated using contour information on bronchial tubes of initial divergence.

That is, the projection point specification unit 15 checks whether a projection image condition that pieces of contour information in the projection images do not overlap each other is satisfied. In a case where the projection image condition is not satisfied (NO in S16), the projection point specification unit 15 changes the projection points on the basis of a preset condition (S18). Further, the projection point specification unit 15 generates a projection image again using contour information at the projection points after the change, checks whether the projection image condition is satisfied, and repeats the change of the projection points and the generation of the projection image until the projection image condition is satisfied. FIG. 8 is a diagram showing a projection image generated using contour information at projection points of a node 123 and a node 119 that satisfy the projection image condition.

Figure 9:
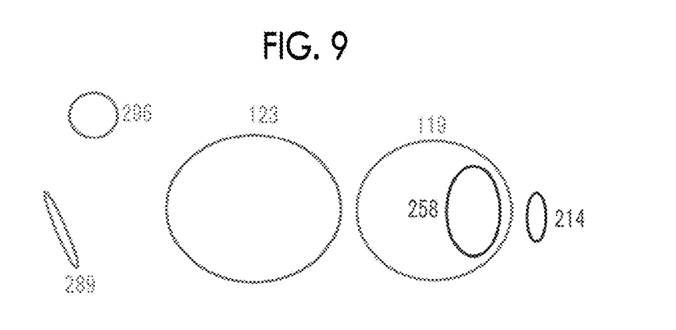
FIG. 9 is a diagram showing an example of a projection image generated so that pieces of contour information do not overlap each other.

Further, with respect to a branch 3 and a branch 4 that are connected to a tip of a branch 1 shown in FIG. 6, and a branch 5 and a branch 6 that are connected to branch 2, similar to the above description, until the projection image condition that pieces of contour information in a projection images do not overlap each other is satisfied, the change of the projection points and the generation of the projection image are repeated. As a result, in a case where a projection image as shown in FIG. 9 is generated, it is preferable that contour information at a node 289 of the branch 4 and a node 296 of the branch 3, protruding from a node 123 of the branch 1 that is a parent branch, and a node 214 of the branch 6 protruding from contour information at a node 119 of the branch 2 that is a parent branch since they are contour information that cannot be seen on an endoscope image obtained by actually imaging the inside of bronchial tubes from the node 80 that is the starting point.

Accordingly, the projection point specification unit 15 specifies, with respect to a child branch, a projection point that satisfies a projection image condition that contour information on the child branch is included in contour information at a node of a parent branch. The projection image condition relating to the child branch is not limited thereto, and for example, even in a case where contour information on a child branch is not included in contour information at a node of a parent branch, in a case where a distance between the contour information at the node of the parent branch and the contour information on the child branch is within a preset threshold value, a corresponding projection point may be remained as a final projection point without being deleted. Specifically, the contour information on the node 214 of the branch 6 shown in FIG. 9 is close to the contour information at the node 119 of the branch 2, and thus, may be remained. Further, even in a case where contour information at a node of a child branch is included in contour information at a node of a parent branch, in a case where the shape of the contour information at the node of the child branch is an ellipse of which the ratio of the minor axis to the major axis is within a preset threshold value like contour information at the node 289 shown in FIG. 9, in a case where the contour information at the node of the child branch cannot be projected, or in a case where the ratio of the size of the contour information at the node of the child branch to the size of the contour information at the node of the parent branch is equal to or smaller than a threshold value and the contour information at the node of the child branch is thus extremely small, the contour information at the node of the child branch may be deleted.

Figure 10:
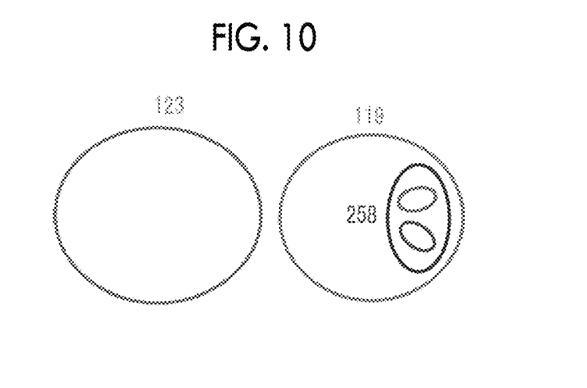
FIG. 10 is a diagram showing an example of a projection image generated using contour information at projection points that are finally specified.

As described above, the change and deletion of the projection points are repeated to satisfy the projection image condition, to then specify final projection points (S20). FIG. 10 is a diagram is a diagram showing a projection image generated using contour information at projection points that are finally specified.

The check of whether the above-described projection image condition is satisfied may be performed using shape information of contour information at projection points. Specifically, as the shape information, diameters (radius, diameter, minor axis, major axis, and the like) of the contour information, a distance between centers, or the like may be used.

In the above description, a configuration in which a projection image is once generated using contour information at projection points that are temporarily specified and a final projection point is specified by checking whether the projection image satisfies a projection image condition may be used, but it is not essential that the projection image is generated, and a configuration in which whether the projection image condition is satisfied on the basis of a positional relationship on a three-dimensional coordinate space of the temporarily specified projection points and the size of the contour information at the projection points may be used.

Further, in the above description, a configuration in which the final projection points are specified by checking whether the contour information at the temporarily specified projection points satisfies the projection image condition may be used, but it is not essential that the projection image condition is checked, and a configuration in which the projection points specified on the basis of the projection point condition in S14 are used as final projection points and a projection image is generated using contour information at the final projection points may be used.

Returning to FIG. 1, the bronchial tube three-dimensional image generation unit 17 performs a volume rendering process with respect to a three-dimensional image acquired in the three-dimensional image acquisition unit 11 to generate a bronchial tube three-dimensional image indicating the shape of a bronchial tube, and outputs the bronchial tube three-dimensional image to the display controller 18.

The display controller 18 causes the display device 20 to display a projection image generated by the projection image generation unit 16 and a bronchial tube three-dimensional image generated by the bronchial tube three-dimensional image generation unit 17.

The display device 20 may include a liquid crystal display, or the like, for example. Further, the display device 20 may be configured as a touch panel, which may be commonly used as the input device 43.

The input device 30 includes a mouse, a keyboard, or the like, and may receive a variety of setting inputs from a user.

According to the endoscope image diagnosis support system of this embodiment, a three-dimensional image obtained by imaging a test object is acquired, a graphical structure of a tubular structure included in the three-dimensional image is generated, and contour information on the tubular structure at each point on the graphical structure is acquired. Further, viewpoint information in the tubular structure is acquired, one point on the graphical structure is specified as a starting point on the basis of the viewpoint information, projection points are specified from the respective points on the graphical structure while following the graphical structure from the starting point, and a projection image obtained by projecting the contour information at the projection points on a two-dimensional plane is generated.

Accordingly, it is possible to generate, through a high-speed process, a projection image in which a direct feature is remained so as to perform a registration process with respect to an endoscope image.

Figure 11:
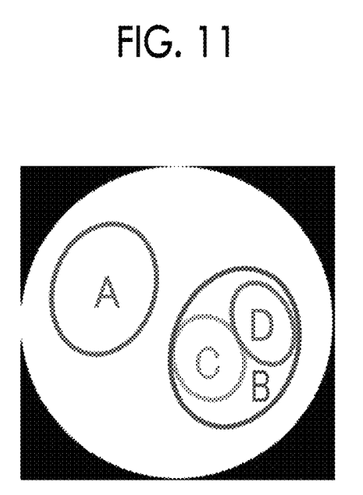
FIG. 11 is a diagram showing a display example in which information on branches is added to a projection image.

Further, in the above-described embodiment, the projection image generation unit 16 may acquire information on branches to which projection points belong, and may add the information on the branches to a projection image, so that the information on the branches can be displayed on the projection image. FIG. 11 is a diagram showing a display example in which "A" to "D" are added as information on branches with respect to a projection image.

Figure 12:
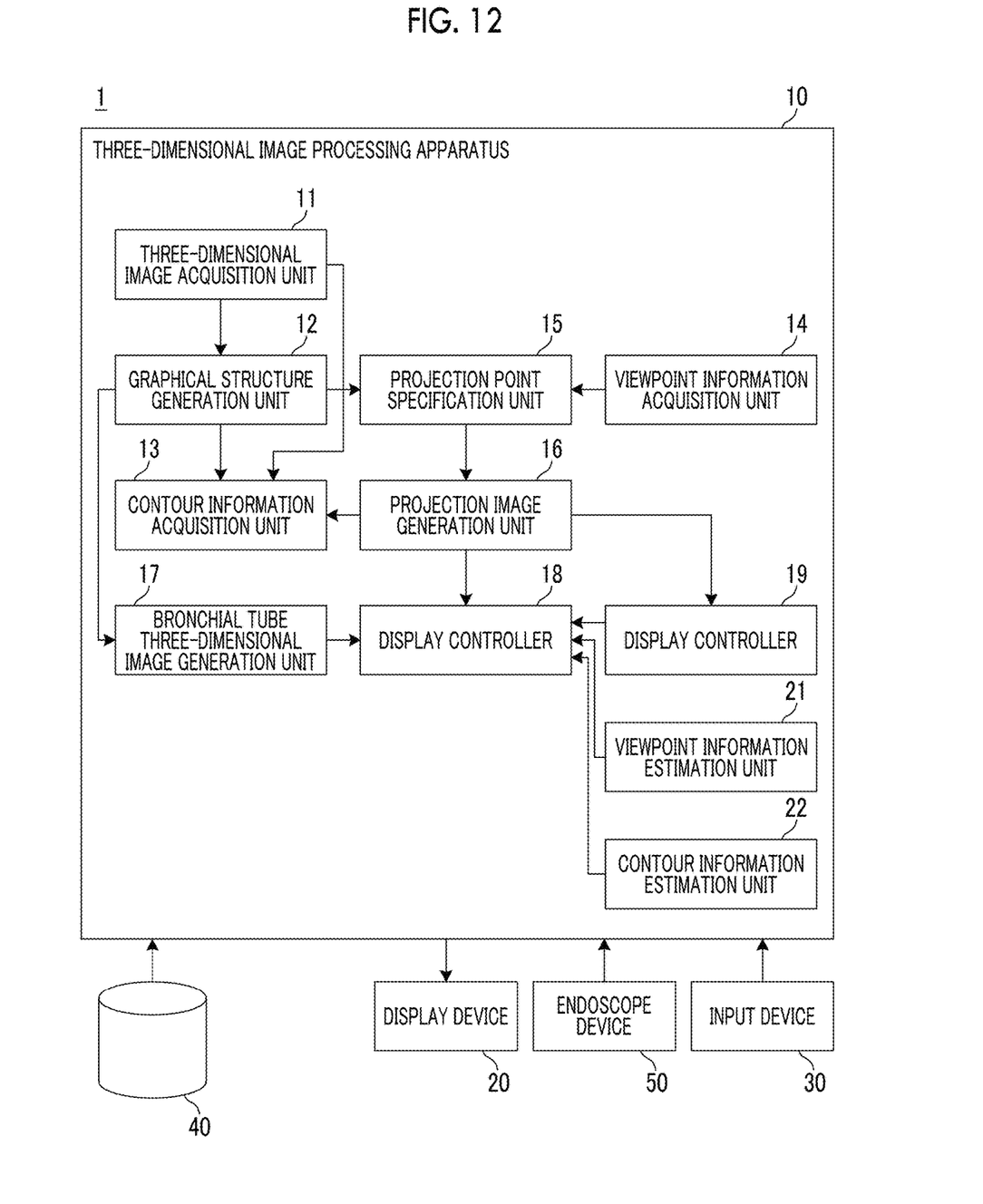
FIG. 12 is a block diagram showing a schematic configuration of an endoscope image diagnosis support system using another embodiment of the three-dimensional image processing apparatus according to the present invention.

In addition, in the above-described embodiment, a configuration in which an endoscope image of a two-dimensional image obtained by actually imaging the inside of a bronchial tube by the endoscope device 50 is further acquired and viewpoint information on the endoscope image (corresponding to a tip position of the endoscope) is estimated on the basis of a relationship between the endoscope image and a projection image may be used. That is, as shown in FIG. 12, a viewpoint information estimation unit 21 may be provided. The viewpoint information estimation unit 21 performs a registration process between a projection image A generated by the projection image generation unit 16 and an endoscope image B output from the endoscope device 50. As the registration process, rigid-body registration or non-rigid-body registration may be used, for example.

Figure 13:
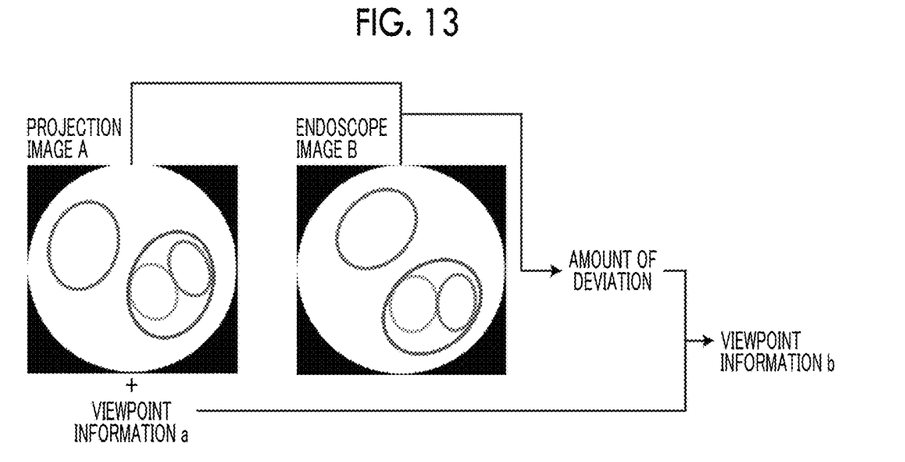
FIG. 13 is a diagram illustrating a method for estimating viewpoint information on an endoscope image on the basis of the amount of deviation between a projection image and an endoscope image, and the viewpoint information on the projection image.

Further, as shown in FIG. 13, the viewpoint information estimation unit 21 estimates viewpoint information b on the endoscope image B on the basis of the amount of deviation between the projection image A and the endoscope image B obtained through the registration process and viewpoint information on the projection image A. It is assumed that the projection image A that is a target of the registration process is generated for each divergent point in a graphical structure, for example, and the viewpoint information b on the endoscope image is estimated on the basis of a projection image A having the smallest amount of deviation among the plurality of projection images A and viewpoint information thereof. As a method for estimating the viewpoint information b on the endoscope image B, for example, in a case where only the size of contour information included in the projection image A and the size of a hole of a bronchial tube included in the endoscope image B are only different, a method for estimating the viewpoint information b by moving viewpoint information a with respect to a projection surface on the basis of a magnification/reduction rate of the size and a distance between the viewpoint information a on the projection image A and the projection surface may be used. The method for estimating the viewpoint information b is not limited to such a method, and may employ various estimation methods based on a geometrical relationship.

The viewpoint information b estimated by the viewpoint information estimation unit 21 may be displayed, for example, as three-dimensional coordinates on the display device 20, or may be displayed on bronchial tube three-dimensional image displayed on the display device 20.

Figure 14:
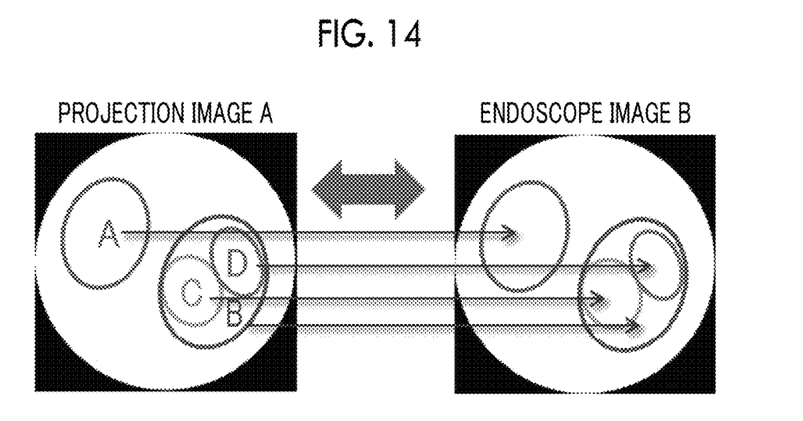
FIG. 14 is a diagram illustrating a method for estimating a hole (contour information) included in an endoscope image corresponding to the contour information included in a projection image.

Further, on the basis of contour information included in a projection image and information on branches added to the contour information, the information on the branches may be added to holes included in an endoscope image output from the endoscope device 50. That is, as shown in FIG. 12, the contour information estimation unit 22 may be provided. Specifically, the contour information estimation unit 22 performs a registration process between the projection image A generated by the projection image generation unit 16 and the endoscope image B output from the endoscope device 50. As the registration process, rigid-body registration or non-rigid-body registration may be used, for example. Further, the contour information estimation unit 22 performs the registration process to estimate holes (contour information) included in the endoscope image B corresponding to the contour information included in the projection image A, as shown in FIG. 14. Further, the contour information estimation unit 22 adds information "A" to "D" on branches added to respective pieces of contour information in the projection image A to corresponding holes included in the endoscope image. The information on the branches added to the respective holes of the endoscope image is displayed on the display device 20 together with the endoscope image, for example.

Figure 15:
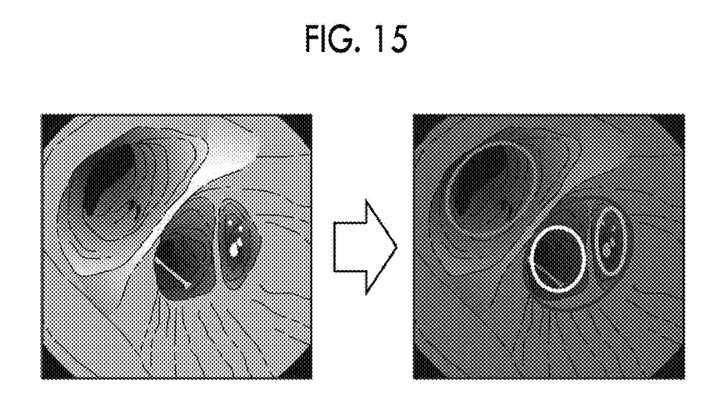
FIG. 15 is a diagram showing an example of a contour image obtained by extracting a contour of a hole from an endoscope image.

Further, in the above description, in a case where the registration process is performed in the viewpoint information estimation unit 21 and the contour information estimation unit 22, an endoscope image output from the endoscope device 50 is used, but the present invention is not limited thereto. Instead, as shown in FIG. 15, a contour image obtained by extracting contours of holes from the endoscope image may be used. As a method for generating the contour image, a method for detecting a region in which pixels of which brightness is equal to or lower than a threshold value are circularly distributed from an endoscope image and extracting a contour of the region as a contour of a hole to generate a contour image may be used.

What is claimed is:

1. A three-dimensional image processing apparatus comprising:
a three-dimensional image acquisition unit that acquires a three-dimensional image obtained by imaging a test object;
a graphical structure generation unit that generates a graphical structure of a tubular structure included in the three-dimensional image;
a contour information acquisition unit that acquires contour information on the tubular structure at each point on the graphical structure;
a viewpoint information acquisition unit that acquires viewpoint information in the tubular structure;
a projection point specification unit that specifies projection points from respective points on the graphical structure on the basis of the viewpoint information and the graphical structure,
wherein the projection point specification unit specifies one point on the graphical structure as a starting point, specifies points included in a preset range as projection candidate points while following the graphical structure from the starting point, and specifies the projection points from the projection candidate points; and
a projection image generation unit that generates a projection image obtained by projecting the contour information at the projection points on a two-dimensional plane.

2. The three-dimensional image processing apparatus according to claim 1,
wherein the projection point specification unit specifies the projection points on the basis of shape information of the contour information.

3. The three-dimensional image processing apparatus according to claim 1,
wherein the projection image generation unit acquires information on branches to which the projection points belong, and adds the information on the branches to the projection image.

4. The three-dimensional image processing apparatus according to claims 1, further comprising:
a viewpoint information estimation unit that estimates, on the basis of a result of a registration process between the projection image and an image different from the projection image and viewpoint information on the projection image, viewpoint information on the different image.

5. The three-dimensional image processing apparatus according to claim 1, further comprising:
a contour information estimation unit that estimates, on the basis of a result of a registration process between the projection image and an image different from the projection image, contour information included in the different image corresponding to the contour information included in the projection image.

6. The three-dimensional image processing apparatus according to claim 4,
wherein the image different from the projection image is a two-dimensional image obtained by imaging the test object.

7. The three-dimensional image processing apparatus according to claim 5,
wherein the image different from the projection image is a two-dimensional image obtained by imaging the test object.

8. The three-dimensional image processing apparatus according to claim 6,
wherein the two-dimensional image is an image captured by an endoscope.

9. The three-dimensional image processing apparatus according to claim 7,
wherein the two-dimensional image is an image captured by an endoscope.

10. The three-dimensional image processing apparatus according to claim 1, further comprising:
a display controller that causes a display device to display the projection image.

11. The three-dimensional image processing apparatus according to claim 1,
wherein the tubular structure is a bronchial tube.

12. A three-dimensional image processing method comprising:
acquiring a three-dimensional image obtained by imaging a test object;
generating a graphical structure of a tubular structure included in the three-dimensional image;
acquiring contour information on the tubular structure at each point on the graphical structure;
acquiring viewpoint information in the tubular structure;
specifying projection points from respective points on the graphical structure on the basis of the viewpoint information and the graphical structure by using a projection point specification unit that specifies projection points from respective points on the graphical structure on the basis of the viewpoint information and the graphical structure,
wherein the projection point specification unit specifies one point on the graphical structure as a starting point, specifies points included in a preset range as projection candidate points while following the graphical structure from the starting point, and specifies the projection points from the projection candidate points; and
generating a projection image obtained by projecting the contour information at the projection points on a two-dimensional plane.

13. A non-transitory computer-readable storage medium storing therein a three-dimensional image processing program that causes a computer to function as:
a three-dimensional image acquisition unit that acquires a three-dimensional image obtained by imaging a test object;
a graphical structure generation unit that generates a graphical structure of a tubular structure included in the three-dimensional image;
a contour information acquisition unit that acquires contour information on the tubular structure at each point on the graphical structure;
a viewpoint information acquisition unit that acquires viewpoint information in the tubular structure;
a projection point specification unit that specifies projection points from respective points on the graphical structure on the basis of the viewpoint information and the graphical structure,
wherein the projection point specification unit specifies one point on the graphical structure as a starting point, specifies points included in a preset range as projection candidate points while following the graphical structure from the starting point, and specifies the projection points from the projection candidate points; and
a projection image generation unit that generates a projection image obtained by projecting the contour information at the projection points on a two-dimensional plane.

* * * * *